(12) United States Patent
Sachdev et al.

(10) Patent No.: US 7,369,331 B2
(45) Date of Patent: May 6, 2008

(54) FIXED FOCUS HANDY OVULATION TESTER

(76) Inventors: Gopal Krishan Sachdev, Kirat Plastics Pvt. Ltd., Vill.Dhumaspur P.O., Badshahpur Sohna Road, Gurgaon, 122-101 (IN); Harinder Preet Singh Bakshi, Kirat Plastics Pvt. Ltd., Vill.Dhumaspur P.O., Badshahpur Sohna Road, Gurgaon, 122-101 (IN)

( * ) Notice: Subject to any disclaimer, the term of this patent is extended or adjusted under 35 U.S.C. 154(b) by 0 days.

(21) Appl. No.: 10/598,150

(22) PCT Filed: Feb. 20, 2004

(86) PCT No.: PCT/IB2004/000461

§ 371 (c)(1),
(2), (4) Date: Jul. 2, 2007

(87) PCT Pub. No.: WO2005/089653

PCT Pub. Date: Sep. 29, 2005

(65) Prior Publication Data

US 2007/0265545 A1    Nov. 15, 2007

(51) Int. Cl.
| | |
|---|---|
| *G02B 27/02* | (2006.01) |
| *A61B 10/00* | (2006.01) |
| *G01N 21/00* | (2006.01) |
| *G01N 33/48* | (2006.01) |
| *G01N 21/03* | (2006.01) |

(52) U.S. Cl. .................. 359/801; 600/551; 422/55; 422/58; 436/63; 436/165

(58) Field of Classification Search ................ 359/396, 359/398, 801, 803, 804; 422/55, 58, 82.05; 436/63, 65, 164; 600/310, 551
See application file for complete search history.

(56) References Cited

U.S. PATENT DOCUMENTS

| | | | | |
|---|---|---|---|---|
| 3,582,181 | A | * | 6/1971 | Manau de Chveca ....... 359/379 |
| 4,815,835 | A | * | 3/1989 | Ortueta Corona .......... 359/379 |
| 5,267,087 | A | * | 11/1993 | Weidemann ................ 359/801 |
| 5,572,370 | A |   | 11/1996 | Cho |
| 6,582,377 | B1 |   | 6/2003 | Van Michaels et al. |
| 6,793,886 | B1 | * | 9/2004 | Weissmahr .................. 422/61 |
| 6,960,170 | B2 | * | 11/2005 | Kuo ........................... 600/551 |
| 2003/0179446 | A1 |   | 9/2003 | Yeh |

FOREIGN PATENT DOCUMENTS

| | | |
|---|---|---|
| WO | WO 98/19797 | 5/1998 |
| WO | WO 99/61891 | 2/1999 |

* cited by examiner

*Primary Examiner*—David N. Spector
(74) *Attorney, Agent, or Firm*—Foley & Lardner LLP (57) ABSTRACT

The present invention provides a fixed focus handy ovulation tester, the said ovulation tester comprising an inner casing (1), having a top and a bottom end; a controllable illuminating assembly (2) located inside the inner casing and near the bottom end of the inner casing and being sealed at the bottom by a bottom face plate (3) and a fixed focus eye piece assembly (4) having a bottom inner portion for placing a biological specimen and a top outer portion for viewing the specimen being removably located at the top end of the inner casing.

6 Claims, 11 Drawing Sheets

FIGURE 4: FIXED FOCUS EYEPIECE ASSEMBLY

FIGURE 5: FIXED FOCUS EYEPIECE ASSEMBLY (a) Perspective view of the
fixed focus eyepiece assembly (b) Sectioned perspective view of
the fixed focus eyepiece assembly (c) Perspective view of lens holder (d) Perspective view of glass holder (e) Perspective view of plano convex lens Plastic lens Plano Plano
polished glass
plate (f) Perspective view of plano
convex field lens (g) Perspective views of single lense magnifier.

FIGURE 6(A): BASIC OPTICAL RAY PATH INSIDE THE EYEPIECE

FIGURE 6(B): BASIC OPTICAL RAY PATH INSIDE SINGLE LENS MAGNIFIER

FIGURE 7: COMPLETE OPTICAL RAY PATH INSIDE THE EYEPIECE SHOWN IN FIGURE 4(A)

FIGURE 8: COMPLETE OPTICAL RAY PATH INSIDE THE EYEPIECE SHOWN IN FIGURE 4(B)

FIGURE 9: COMPLETE OPTICAL RAY PATH INSIDE THE EYEPIECE HAVING BI-CONVEX LENS

FIGURE 10: PRODUCT ASSEMBLY OF THE FISED FOCUS HANDY OVULATION TESTER

PRODUCT ASSEMBLY (A)

(B)

SECTION B-B (C)

SECTION A-A

FIG.11

FIXED FOCUS HANDY OVULATION TESTER

FIELD OF THE INVENTION

The present invention relates to a portable microscope apparatus having fixed focus for the indicating woman's fertility period during her menstrual cycle. More particularly, the present invention relates to a fixed focus handy ovulation tester which obviates the procedure of manual focusing and renders improved image clarity, contrast and increased depth of focus. The fixed focus handy ovulation tester of the present invention effectively eliminates spurious images, which cause confusion in accurately ascertaining the results. Also, the reliability of the eyepiece over longer periods of usage is ensured because of its sealed construction.

BACKGROUND AND PRIOR ART DESCRIPTION

It has been clearly established that women's saliva during her menstrual cycles can be used to determine their fertile period. Scientists have observed a clear difference in the cell pattern in saliva between fertile and sterile periods. More particularly, scientists have found that during a woman's fertile period, a sample of dried saliva forms vein-like structure or fern leaf like pattern. Contrary to the above, during sterile periods, the dried saliva sample typically forms a spotted or a dot like pattern.

In order to administer self-examination, special optical devices such as microscopes or magnifying glasses are available in the market.

U.S. Pat. Nos. 4,815,835 and 5,267,087 which are incorporated herein as reference describe such handy ovulation tester devices. The handy ovulation testers prepared in accordance with the teachings of the aforesaid documents and those existing in the market have certain shortcomings such as the lack of clarity of the image. The clarity of the image apparent to the user is very much wanting at times, so the user often lacks some degree of confidence in her observation. In order to obviate such shortcomings, efforts have been made in the present invention to improve the clarity of image by certain built-in quality and optical design features, which are simple and do not change their form or cost materially.

In erstwhile ovulation testers, the eyepiece needs to be focused by screwing or pushing the eye piece lens part, which is usually called an outer part with respect to an inner part to see or magnify the object (biological specimen such as dried saliva) clearly. This approach of focusing is cumbersome from the point of view of users who will have to be made aware of this technique before use. This approach often causes some strain to the eye besides manual effort.

Constructionally, the prior art devices comprise of inner and an outer telescopic tubes which are configured to move in and out with respect to each other. The eyepiece is incorporated at the top end of one of the telescopic tubes (preferably the inner tube) and the other telescopic tube (preferably the outer telescopic tube) is provided with a provision to accommodate a slide having the biological specimen thereupon. A light source is located opposite to the end having the eyepiece so as to illuminate the biological specimen. The light source can be a bulb or LED. The inner and the outer tubes are moved with respect to each other in order to achieve focusing on the slide having the biological specimen. Due to the telescopic construction of the tubes, the eye piece and the object (the biological specimen) are aligned in different planes for focus and hence the probability of error/unclear image increases for want of coaxiality in lens and surface of object.

In existing focusable devices, one tube containing lenses and the other one containing object surface are either pushed or turned against each other, thus creating the focusing effect. However as the time passes, the areas that are pushed or rotated get worn out causing difficulty to accurately adjust the focus of the device. Also, it is observed that by the action of pushing or rotating the telescopic tubes, dust particles generated due to the rubbing action of the moving parts fall on the enclosed optical surface and onto the opposite surface of the glass plate wherein the biological specimen is applied. Settlement of these dust particles causes spurious shadows on the image and adversely affects the contrast and sometimes confuses the user.

Further due to the two-piece construction, the inventors have very often observed that the moisture from the environment and even very fine dust particles enters into the eyepiece and hamper the quality of the image.

Even when we look into manufacturing a set of telescopic tubes which are accurately co-axial and which do not have minimum gap between them, it can be a complex task. To avoid misalignment of the telescopic tubes, special materials are required to be provided between them.

Further, looking into the cost of such a telescopic device, due to the complexity in the manufacturing process of these devices and the amount of special devices to be used for obtaining the alignment of the telescopic tubes, the cost of manufacturing is substantially high.

Thus, there appears a necessity to develop an improved and handy portable microscope apparatus for viewing biological specimens such as saliva for the detection of woman's fertility period during her menstrual cycle, having fixed focus that overcomes the disadvantages discussed above.

OBJECTS OF THE PRESENT INVENTION

The main object of the present invention is to provide a portable microscope apparatus having fixed focus.

Another object of the present invention is to provide a fixed focus handy ovulation tester which obviates the disadvantages described above and especially obviates the procedure of manual focusing and renders improved image clarity, contrast and increased depth of focus.

SUMMARY OF THE INVENTION

The present invention provides a fixed focus handy ovulation tester, the said ovulation tester comprising an inner casing (1), having a top and a bottom end; a controllable illuminating assembly (2) located inside the inner casing and near the bottom end of the inner casing and being sealed at the bottom by a bottom face plate (3) and a fixed focus eye piece assembly (4) having a bottom inner portion for placing a biological specimen and a top outer portion for viewing the specimen being removably located at the top end of the inner casing.

BRIEF DESCRIPTION OF THE ACCOMPANYING DRAWINGS

In the drawings accompanying the specification,

FIG. 3 (a) represents the front view of the inner casing with the self locating and holding rib.

FIG. 3 (b) represents the perspective view of the inner casing with the self locating and holding rib.

FIG. 3 (c) represents the side view of the inner casing with the self locating and holding rib.

FIG. 4 (a) represents the sectioned view of the fixed focus eyepiece assembly prepared in accordance with a first embodiment of the present invention which incorporates a plano-convex eye lens in the eye holder assembly and a hemispherical or hyper hemispherical plano-convex field lens in the glass holder assembly.

FIG. 4 (b) represents the sectioned view of the fixed focus eyepiece assembly prepared in accordance with a second embodiment of the present invention which incorporates a combination of a plano-plano glass plate and a plano-convex eye lens in the eye holder assembly and a combination of a plano-convex field lens and a plano-plano glass plate in the glass holder assembly respectively.

FIG. 4 (c) represents the sectioned view of the fixed focus eyepiece assembly prepared in accordance with a third embodiment of the present invention which incorporates a combination of a plano-plano polished glass plate and a plano-convex eye lens of transparent plastic material in the eye holder assembly; and a bi-convex lens (glass or plastic) and a plan-convex field lens which may consist of glass or a combination of plastic lens cemented with plano-plano polished glass plate.

FIG. 4 (d) represents the sectioned view of the fixed focus eyepiece assembly prepared in accordance with a fourth embodiment of the present invention which incorporates a single plano-convex rod lens as both an eye lens and a field lens.

FIG. 5 (a) shows the perspective view of the fixed focus eyepiece assembly prepared in accordance with the present invention.

FIG. 5 (b) shows the sectioned perspective view of the fixed focus eyepiece assembly prepared in accordance with the present invention.

FIG. 5 (c) shows the perspective view of the lens holder prepared in accordance with the present invention.

FIG. 5 (d) shows the perspective view of the glass holder prepared in accordance with the present invention.

FIG. 5 (e) shows the perspective view of the plano-convex eye lens used in accordance with the teachings of the present invention.

FIG. 5 (f) shows the plano convex field lens.

FIG. 5 (g) shows perspective view of single lens magnifier.

FIG. 6 (a) shows the basic optical ray path. As can be seen from the optical ray path, the focal plane of the eyepiece coincides with the plane on which the biological specimen is applied.

FIG. 6 (b) shows a typical single lens magnifier (which consists of a single plano-convex rod lens, where the flat surface lies on the focus of this lens) where the saliva is applied on its flat surface, and it is observed from the curved surface side, and is built into the device as an eyepiece.

FIG. 10 (a) shows the bottom view of the fixed focus handy ovulation tester.

FIG. 10 (b) shows the B-B section of the fixed focus handy ovulation tester of the present invention.

FIG. 10 (b) shows the A-A section of the fixed focus handy ovulation tester of the present invention.

DETAILED DESCRIPTION OF THE INVENTION

Accordingly, the present invention provides a fixed focus handy ovulation tester, the said ovulation tester comprising:
an inner casing (1) having a top and a bottom end;
a controllable illuminating assembly (2) located inside the inner casing and near the bottom end of the inner casing and being sealed at the bottom by a bottom face plate (3), and
a fixed focus eye piece assembly (4) having a bottom inner portion for placing a biological specimen and a top outer portion for viewing the specimen being: removably located at the top end of the inner casing.

In an embodiment of the present invention, the fixed focus handy ovulation tester is further provided with an outer case (5) for protection.

In another embodiment of the present invention, an inner surface OF the outer case is provided with an outer case sleeve (11).

In yet another embodiment of the present invention, the inner casing is provided with a self locating and holding rib (21) at a substantially lower portion for conveniently guiding and holding the outer case to the inner casing.

In still another embodiment of the present invention, the fixed focus eye piece assembly comprises of a sealed housing (111) having a viewing slot (112) at a top end and incorporated with a single plano-convex rod lens (113), wherein the focus of the rod lens lies on a flat surface (114) of the same whereupon the biological specimen is applied.

In one more embodiment of the present invention, the fixed focus eye piece assembly comprises of a glass holder assembly (33) integrated with a lens holder assembly (31), wherein the glass holder assembly and the lens holder assembly are maintained at a predetermined distance by a separating means (32).

In one another embodiment of the present invention, the glass holder assembly is constituted as a sub assembly comprising of a housing (36) fitted with a Plano-convex field lens (37) having a curved surface and a flat surface, wherein the flat surface acts as an object surface where upon the biological specimen is located/applied.

In a further embodiment of the present invention, the thickness of the Plano convex field lens is equal to or greater than the radius of the lens such as a hyper hemispherical lens or a rod lens In a further more embodiment of the present invention, the Plano convex field lens is made of glass or is made of transparent plastic (37) glued using transparent optical cement to Plano-Plano glass plate (38), thereby compensating the adverse effect of plastic surface deviation/warping of flat glued surface and serving as a hard glass surface for application of biological specimen to enable repeated application and cleaning.

In another embodiment of the present invention, the glass holder assembly is constituted as a sub assembly comprising of a housing (36) fitted with a bi-convex lens (43) and a Plano-convex field lens (42), wherein the biconvex lens is placed above a curved surface of the field lens and the flat surface acts as an object surface where upon the biological specimen is located/applied.

In yet another embodiment of the present invention, the lens holder assembly is constituted as a sub assembly comprising a housing (34) fitted with a Plano convex eye lens (35).

In still another embodiment of the present invention, the eye lens is made of transparent plastic (35) and is glued using transparent optical cement to Plano-Plano polished glass plate (38), serving to compensate for the adverse optical effect plastic surface deviation/warping and offering a hard exterior glass surface to enable cleaning.

In one more another embodiment of the present invention, in the fixed focus eyepiece assembly the number of Air to glass surfaces is restricted to four, including the surface on which the biological specimen is smeared for observation.

In one another embodiment of the present invention, the glass holder assembly (33), the lens holder assembly (31), and the separating means (32) are sealed to form the fixed focus eyepiece.

In a further embodiment of the present invention, a metal sleeve (51) is further provided inside the inner casing.

In a further more embodiment of the present invention, the controllable illuminating assembly comprises of a light source (52), an associated power supply means (53) and a switch means (54).

In another embodiment of the present invention, the light source means is selected from the group comprising of a bulb and LED.

In yet another embodiment of the present invention, the power Supply is a battery, wherein the battery is a pencil-cell battery or a button cell battery.

In still another embodiment of the present invention, the LED is masked by a diaphragm (55), the diameter of the diaphragm is 1.6 mm.

In one more embodiment of the present invention, the fixed focus handy ovulation tester further comprises of a holder (56) for holding the battery and the LED.

In one another embodiment of the present invention, the biological specimen is saliva.

Figure 4:
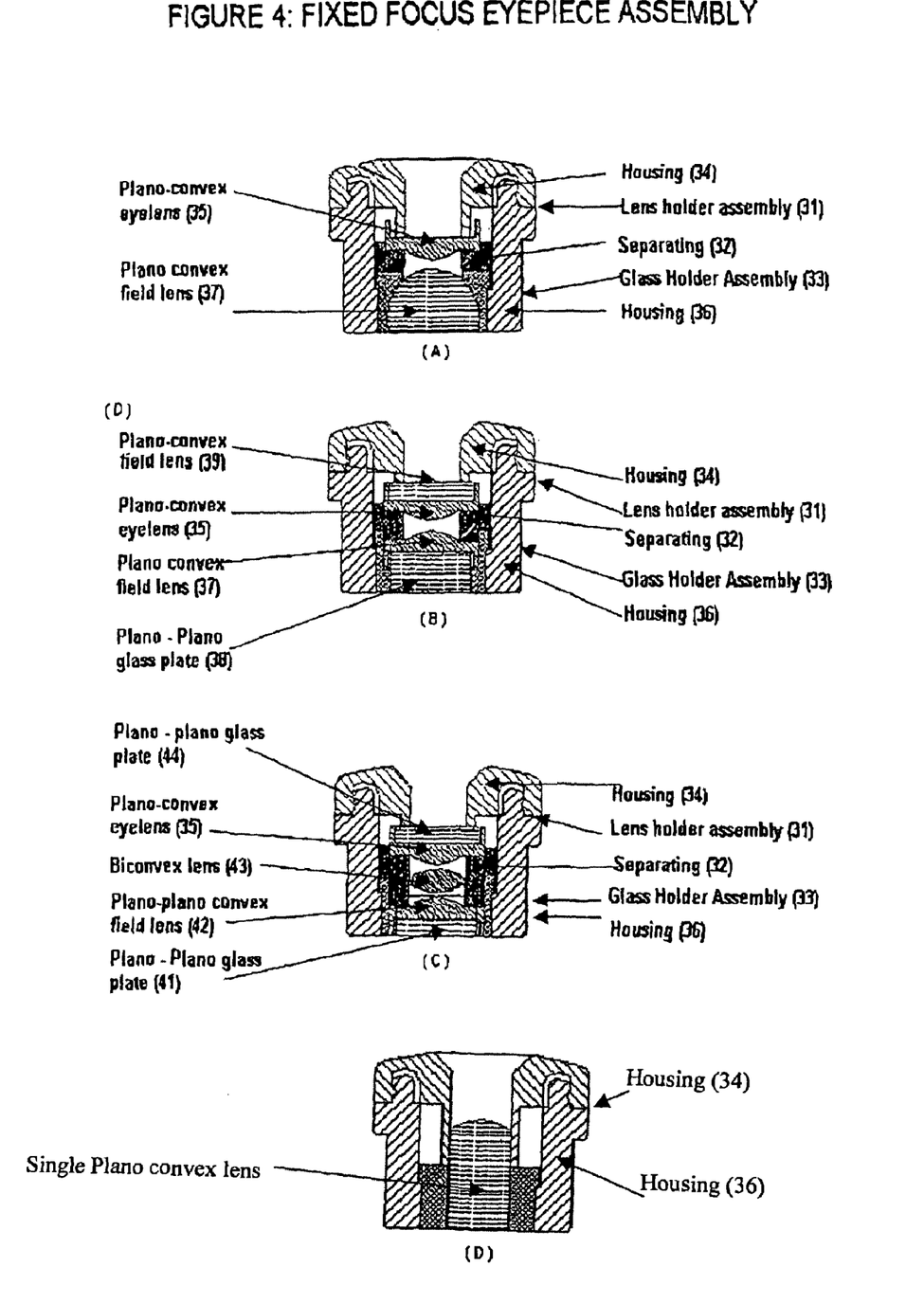
Figure 5:
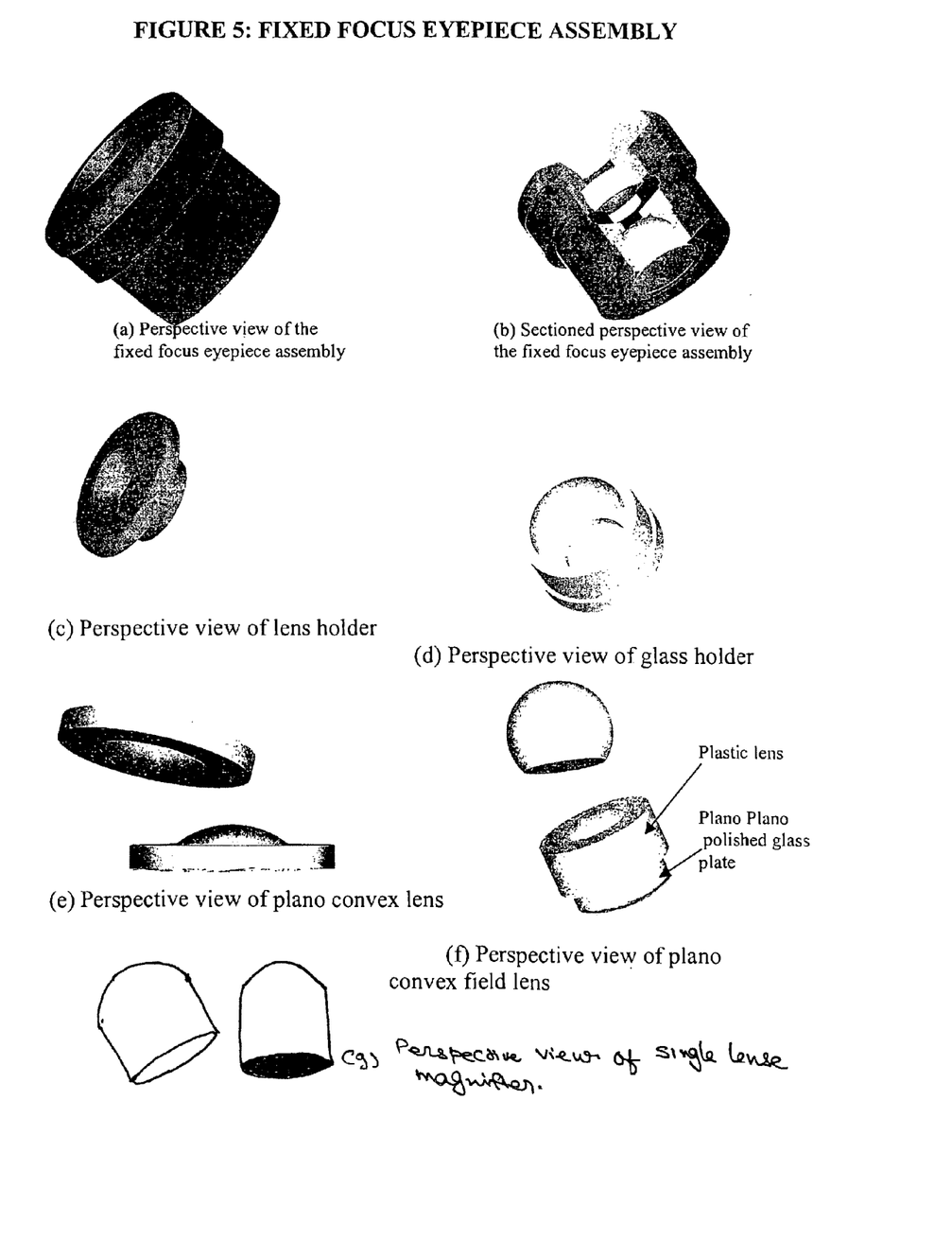

The high magnification eyepiece used in the Handy Ovulation Tester of the present invention consists of a plano-convex lens and a thick plano-convex field lens as can be seen from FIG. 4 (a). According to a preferred embodiment of the present invention, the field lens has been made unusually thicker, wherein the thickness of the field lens is equal or greater than the radius of the lens, like a hemisphere or hyper-hemispherical lens. The biological specimen, i.e. the saliva is smeared on the plane surface of this field lens, which also forms the focal plane of the eyepiece, as in FIG. 6. The LED is covered with a diaphragm of nearly 1.6 mm diameter aperture, refer to any one of FIGS. 7 to 9.

The invention is further described with reference to the preferred embodiment which are given by way of illustration only and should not be construed to limit the scope of the invention in any manner. It can clearly be understood by a person skilled in the art that the description given below merely illustrates some of the preferred features of the present device. Additional modifications and improvements utilizing the teachings of the present invention can be readily anticipated by such skilled person.

Figure 11:
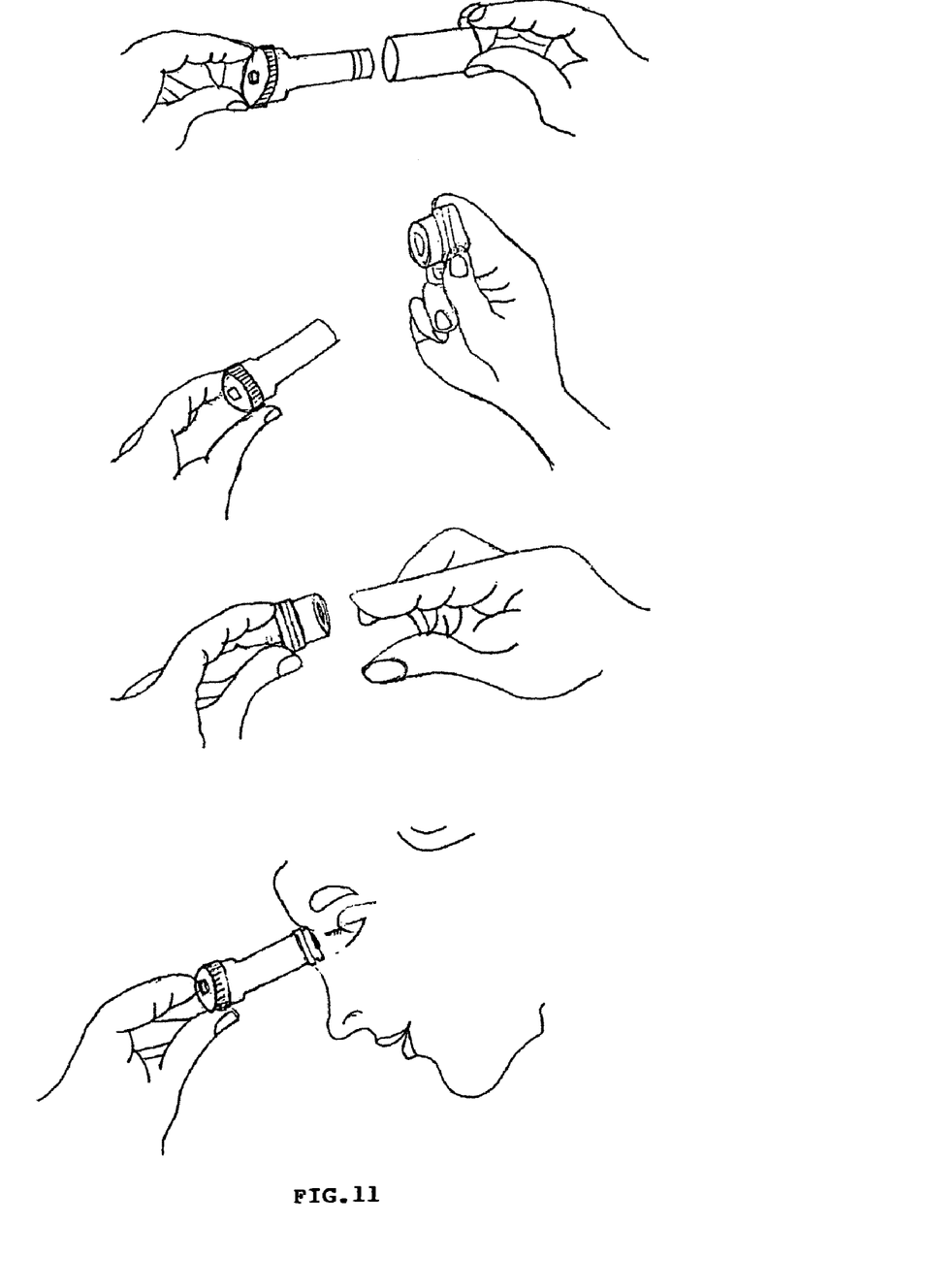
FIG. 11 shows the procedure for operating the device of the present invention. As can be seen from this figure, the user is not required to do any manual focusing to perform the ovulation test.

The device is fixed focus, and does not need manual focusing as can be seen from FIG. 11 which shows the procedure for operating the device of the present invention. The diaphragm masking the LED cuts off unnecessary light, enhances the contrast and increases depth of focus of the eyepiece as a consequence of reduced Exit Pupil aperture (image of the diaphragm formed by the eyepiece). The increased depth of focus in the present invention accommodates for dioptric variations up to plus/minus 4 diopters, for long and short sighted user's unaided eye. In this proposed optical scheme, the diaphragm serves as the entrance pupil and its image formed by the Eyepiece is the Exit Pupil of the system. When the diaphragm is 1.6 mm diameter; and the Eyepiece focal length is 4 mm; and the distance between the Eyepiece and the diaphragm is 20 mm, the size of the Exit Pupil will be around 0.4 mm.

The contrast/clarity of the image is improved by using a thicker field lens (which reduces spherical aberration, since there is a larger length of denser medium in the path of convergent beam of light).

Figure 6A:
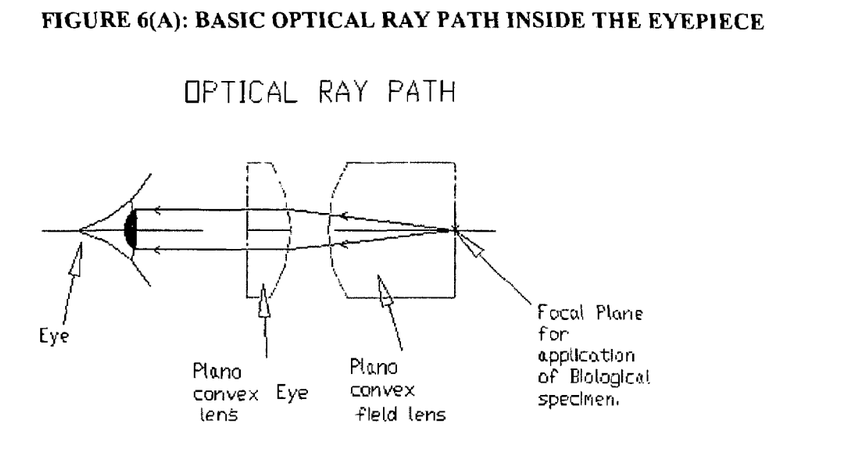
Figure 6B:
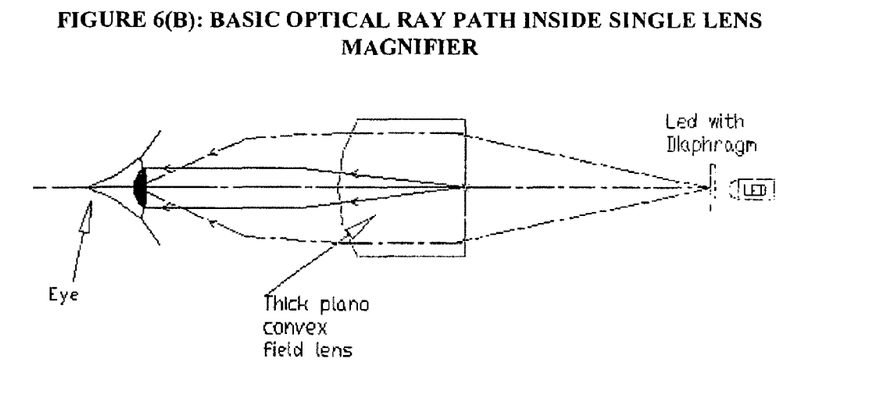
Figure 7:
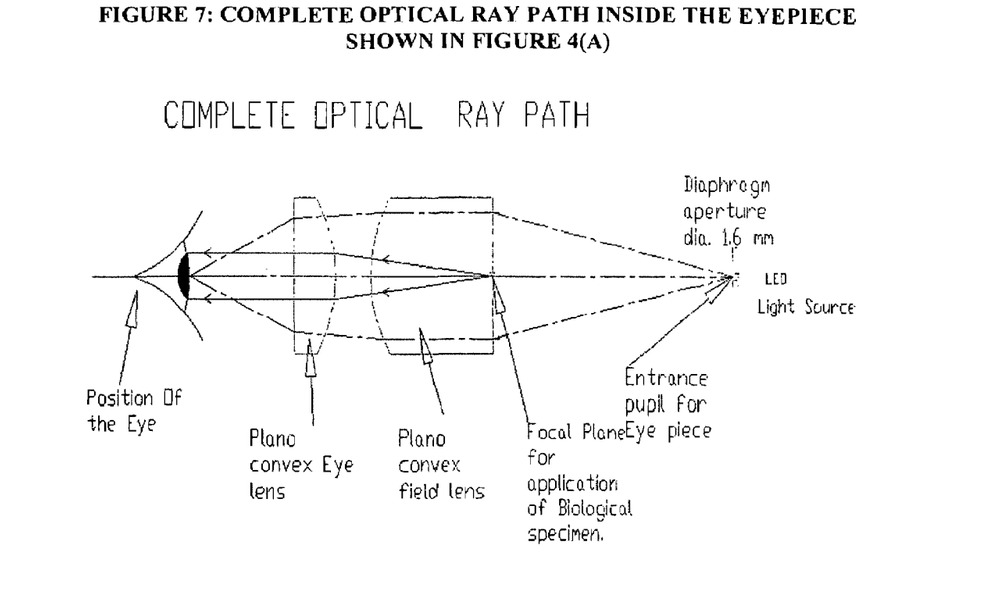
FIG. 7 represents the complete optical ray path taking place inside the device of the present invention. This complete optical ray path corresponds to a fixed focus eyepiece assembly as shown in FIG. 4 (a). The placement of the diaphragm and its aperture are clearly shown in FIG. 7.
Figure 8:
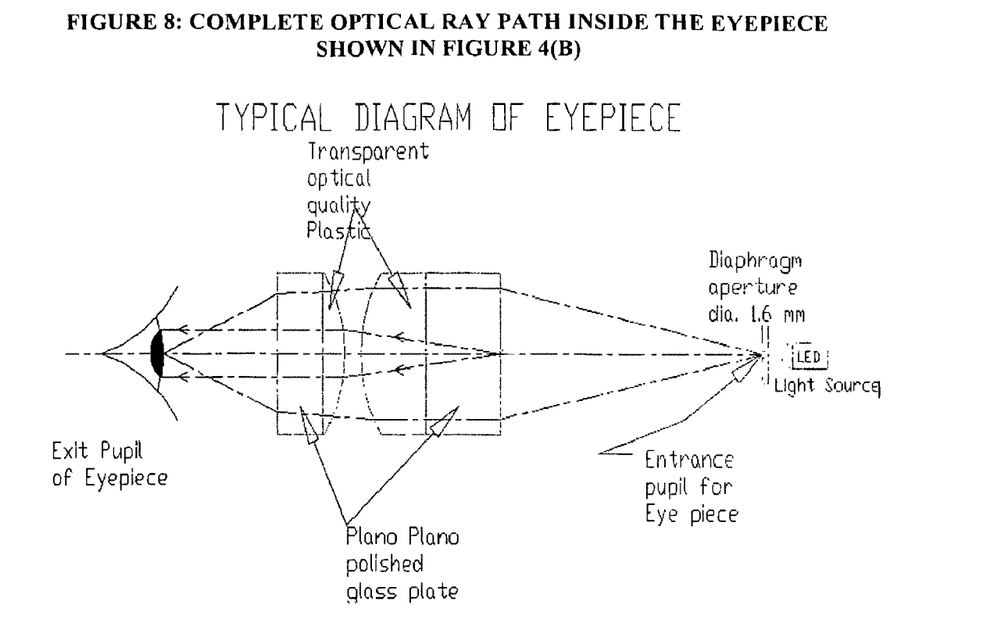
FIG. 8 represents the complete optical ray path talking place inside the device of the present invention. This complete optical ray path corresponds to a fixed focus eyepiece assembly as shown in FIG. 4 (b). The placement of the diaphragm and its aperture are also shown in this figure.
Figure 9:
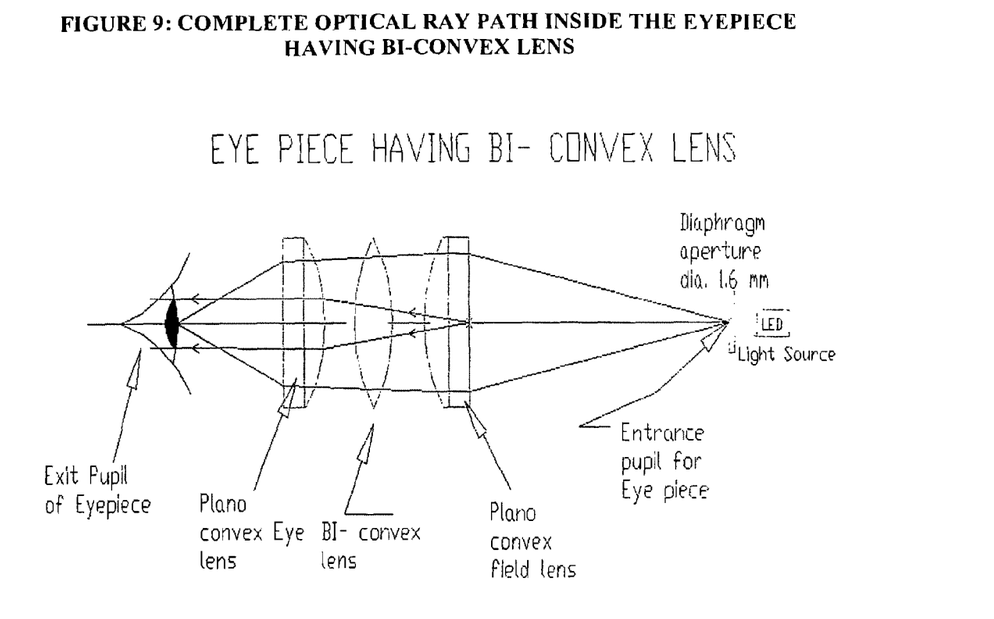
FIG. 9 represents the complete optical ray path taking place inside the device of the present invention. This complete optical ray path corresponds to a fixed focus eyepiece assembly as shown in FIG. 4 (c). The placement of the diaphragm and its aperture are also shown in this figure.

The contract/clarity of image is improved by reducing the number of Glass-to-Air reflections, since only four Glass-to-Air surfaces are involved in the device of the present invention. In one of the simplest forms, according to a preferred embodiment of the present invention, the number of Air-to-Glass or lens surfaces have been reduced to four which includes the focal plane surface of the field lens where the biological specimen i.e. the saliva is applied as shown in FIGS. 6 to 8. Some products in the market do have foul Air-to-Glass surfaces, however, they consist of a double convex lens and a thin plano-plano glass plate for application of saliva. It has been noticed that these products have poor image quality because of large spherical aberration, and curvature of field inherent in such system of single lens. Besides the other side of thin plano-plano plate (for application of saliva) is quite close to the focal plane and hence, any condensation or settlement of dust on it impairs the clarity of the image. Also, it has been noticed that such devices are neither sealed nor have fixed focus.

The saliva is smeared on the flat surface of the flat surface of the field lens. (According to the present invention, the eyepiece is adjusted and focused at the plane meant for smearing of saliva. That is, on to the outer Plano surface of the thicker Field lens. This reduces the number Glass-to-Air Surfaces to four), FIG. 6, 7, 8.

Confidence of the user is boosted by the optical construction of the present invention since her clarity of vision is not spoiled by spurious shadows due to condensation and dust on the other (curved) surface. The curved surface of the thicker Field Lens is at considerable distance from the focal plane (Plan) surface of the Field Lens, and therefore any dust or blemishes on the surface of the Field Lens are out of focus while viewing through the eyepiece as can be seen in FIGS. 6 to 8.

To make the device economically viable and high quantity productive, the convex lenses have been replaced by transparent plastic materials instead of glass (refer to FIG. 8).

Further a special transparent adhesive has been used to stick plastic lenses to plano-plano polished glass plates, eliminating aberrations occurring due to inherent quality of plastics to shrink on solidification.

The eyepiece of the device is based on an optical system which has reduced spherical aberration, because of thicker field lens. The numerical data illustrating the reduction in the spherical aberration in the device is as follows:

Equivalent Focal Length of the Eyepiece=4.16 mm
Magnification of the Eyepiece=60.14×
Radius 1=Infinite (flat)
Radius 2=3.89 mm
Radius 3=3.89 mm
Radius 4=Infinite (flat)
Center Thickness of Eyelens=1.6 mm
Air Gap Between Eyelens and Fieldlens=1 mm
Refractive Index of Glasses=1.5
For Relative Aperture of f/2:
Spherical Aberration=0.217 mm when Center Thickness of Fieldlens=1.6 mm
Spherical Aberration=0.176 mm when Center Thickness of Fieldlens=5.17 mm It is intended to make the Center Thickness of the Fieldlens so large that its outer surface lies on the focus of the system (where the saliva can be smeared) as shown by ray path in FIGS. 6 to 8.

In the device of the present invention the saliva is smeared on the flat surface of thicker Plano convex field lens which is of hemisphere or hyper hemisphere or rod lens form. The optical design of the eyepiece is so computed aid adjusted that its focus is at the plane meant for the smearing of the saliva, i.e. on to the outer surface of the field lens. In the device of the present invention, the number of Glass (or refracting medium) to Air Surfaces has been reduced and so also the internal reflection by eliminating separate plano-plano glass plate for application of smear. Comparing with the existing devices, it can be seen that the device of the present invention provides a saving of 4% loss on each surface, i.e. amounting to 8% because of elimination of two surfaces.

It is a well known scientific phenomena that when light passes from transparent lighter medium to transparent denser medium, or vice versa, a fraction of the light, nearly 4%, gets reflected, depending upon the difference in the refractive indexes between the two mediums. In order to reduce large portion of thus reflected light, the surfaces are usually given anti-reflection coatings wherever economics/quality requirements necessitate. It is desirable to reduce this reflected light from glass to air surfaces, which otherwise scatters itself onto the image, and dilutes the contrast of the object/image. The inventors in the present invention have therefore structured the optical system of the device (eyepiece) in such a way that the number of glass to air surfaces are reduced to minimum. That is, four only in this case, including the surface on which saliva is smeared, as apparent in FIGS. 6-8.

It can be clearly noticed from any one of FIGS. 6 to 8 that the other surface of the smeared optical component is distant enough to be completely and very much out of focus of the eyepiece. The Applicants have specially sealed the interiors of the eyepiece to protect it from condensation and dust and is waterproof.

To prolong the reliability of the device, the applicants have eliminated the focusing mechanism which is otherwise prone to wear and tear. The sealing of the eyepiece and elimination of the focusing mechanism increases confidence of the user in using the device of the present invention, FIGS. 4 (*a*) to (*c*) and 5 (*a*) to (*f*). The confidence in the device is reposed by offering consistent clarity of image.

In erstwhile designs, while trying to focus and see the saliva patterns, the user sees in-focus and out-focus images, which differ slightly. Thus the impression of the image varies, and the user's interpretations keep changing. There is no such change involved in the present invention, since it's a fixed focus design, and thus the impression of the user is always consistent.

In the present invention, the applicants have masked the LED by a diaphragm of 1.6 mm diameter. This reduces diameter of the Exit Pupil, thereby increasing depth of focus. It also reduces stray light. Reducing the aperture in general, increases the depth of optical focus. This is a well known optical principle which is well known in its simplest form in a pin hole camera. The smaller the size of the pin hole, the longer the range of objects, from near to far, which can get imaged on its screen. In our invention, we have reduced the size of the Exit Pupil (which is the entrance pupil for the eye), and the screen is the retina of the user.

Figure 10:
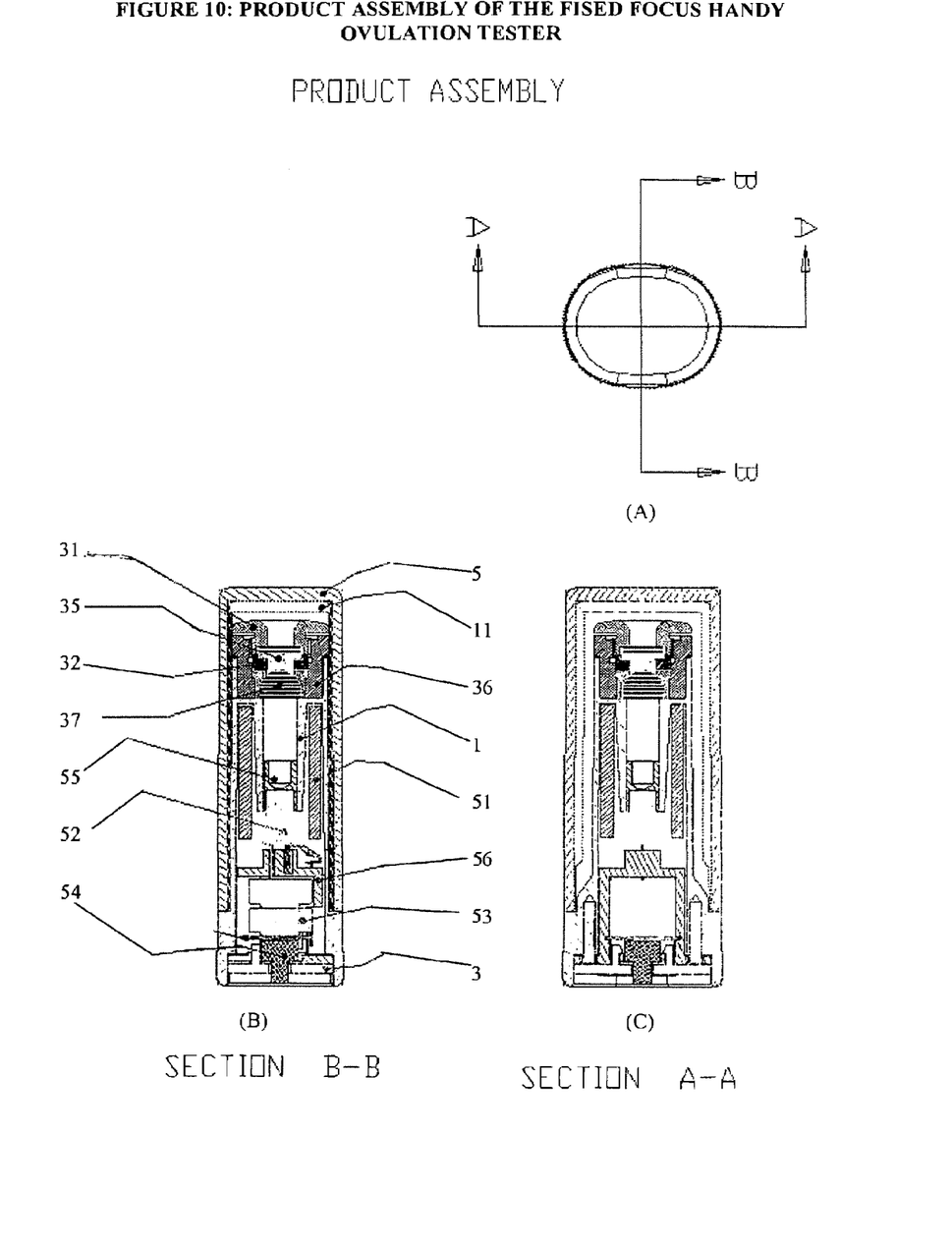

Without deviating from the true sense of the present invention, the Applicants would like to emphasize that field lens can be made of glass, or it may be made of transparent plastic, and glued with transparent optical cement to plano glass blank, serving multiple purposes—viz., compensating the adverse optical effect of plastic surface deviations/warping of flat/glued surface; and serving a hard glass surface for application of saliva smear to enable repeated application and cleaning as can be seen from FIGS. 10 (*a*), (*b*) and (*c*).

The eye lens can also be made of transparent plastic, and glued with transparent optical cement to plano-plano glass blank, serving to compensate for adverse optical effect plastic surface deviation/warping, and offering a hard exterior glass surface to enable necessary cleaning.

Figure 3A:
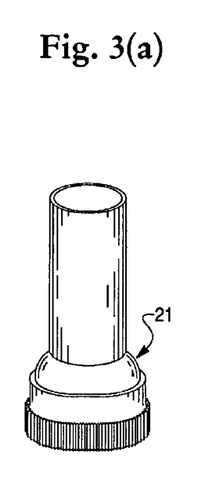
Figure 3B:
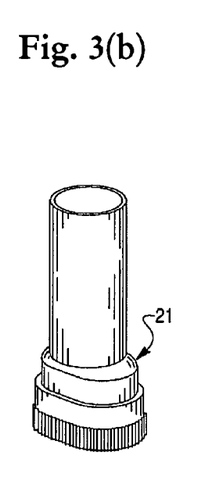
Figure 3C:
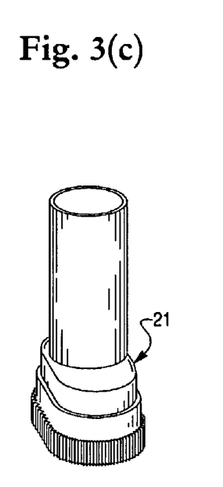

It can be clearly noticed from FIGS. 3 (*a*) to (*c*) that the self locating and holding rib provided at a substantially lower portion on the inner casing not only helps in conveniently guiding and holding the outer case on to the inner casing but also provides a esthetic appeal to the inner casing.

Figure 1:
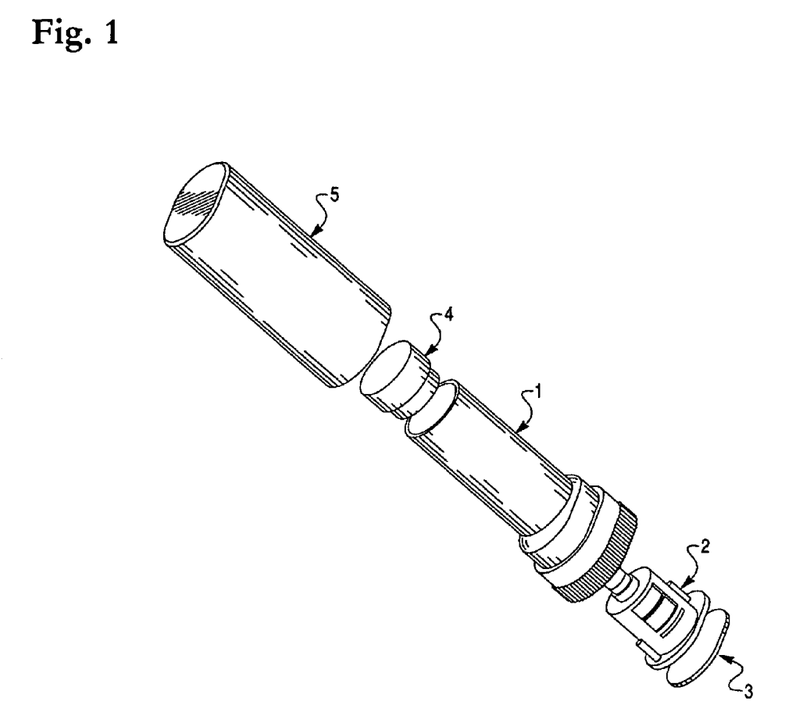
FIG. 1 depicts the exploded view of the fixed focus handy ovulation tester.
Figure 2:
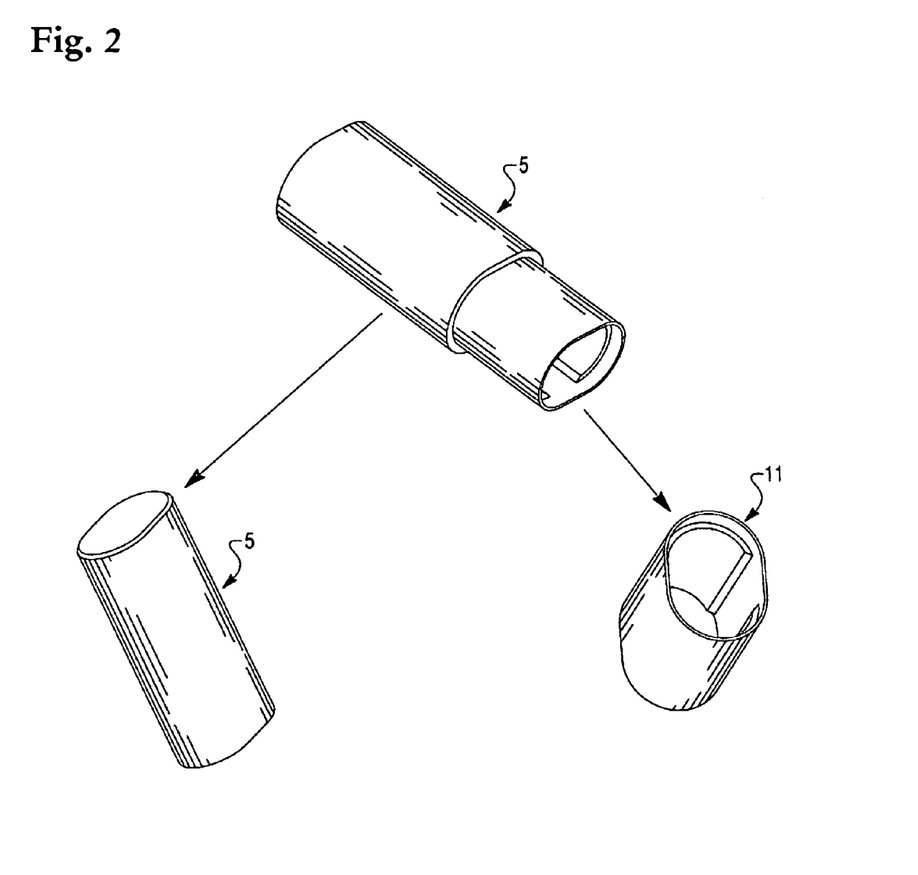
FIG. 2 represents the outer case used in the present invention to cover the fixed focus handy ovulation tester.

The outer case is provided with a outer case sleeve as can be seen from FIG. 2 to avoid scratching the inner casing.

For operating the device for testing the ovulation, the following foul steps are performed as illustrated in FIG. 11:

Step 1: The outer casing is removed.

Step 2: The fixed focus eyepiece assembly is carefully removed from the top end of the inner casing.

Step 3: Smearing of saliva on the bottom inner portion of the fixed focus eyepiece assembly. The bottom inner portion of the fixed focus eyepiece assembly is made flat specifically for this purpose. The saliva is then allowed to dry for a few of minutes. After the saliva gets dried, the fixed focus eyepiece assembly is carefully placed on the top end of the inner casing.

Step 4: Push the button provided at the bottom of the device and look through the top outer portion of the fixed focus eyepiece to see the image. In this final stage, no focusing is done. In fact, there is no provision for focusing provided in the device of the present invention.

The advantages of the present invention is described here below:

1. A Handy Ovulation Tester, which is fixed focus and does not need manual focusing.
2. The optical system has enough depth of focus, and adjusted taking care of dioptric variations of about plus/minus 4 diopters of the user's unaided eye.
3. The eyepiece of the device is based on an optical system which has reduced spherical aberration, because of thicker field lens.

4. The optical design of the eyepiece is so computed and adjusted that its focus is at the plane meant for the smearing of the saliva, i.e. on to the outer surface of the field lens.
5. The number of Glass (or refracting medium) to Air Surfaces has been reduced and so also the internal reflection by eliminating separate plano-plano glass plate for application of smear.
6. The other surface of the smeared optical component is distant enough to be completely and very much out of focus of the eyepiece.
7. The interior of the eyepiece is sealed to protect it from condensation and dust and is waterproof.
8. The reliability/life of the device is prolonged by eliminating the focusing mechanism which is otherwise prone to wear and tear.
9. Confidence in the device is reposed by offering consistent clarity of image.
10. The LED is masked by a diaphragm of 1.6 mm diameter. This reduces diameter of the Exit Pupil, thereby increasing depth of focus. It also reduces stray light.

The invention claimed is:

1. A portable ovulation testing apparatus comprising: an inner casing having top and bottom ends; a controllable illuminating assembly comprising an LED masked with a diaphragm disposed at the bottom end of the inner casing, the assembly being covered at the bottom by a base plate; and a sealed fixed focused eyepiece assembly removeably disposed at the top end of the inner casing, wherein said eyepiece assembly is used for magnified viewing of a biological specimen, and wherein said assembly further comprises of a bottom portion for receiving the biological specimen, and top portion for viewing the biological specimen.

2. The portable ovulation testing apparatus as claimed in claim 1, wherein the fixed focus sealed eyepiece assembly comprises of a combination of a plano-convex eye lens on top, and a substantially thicker plano-convex field lens at the bottom; the convex surfaces of the eye lens and field lens being inwardly disposed and facing each other with their respective plano surfaces outwardly disposed; and wherein the plano surface of the field lens is coincident with the focal plane of the eyepiece, assembly in an arrangement wherein the plano surface of the field lens provides an object surface upon which the biological specimen is disposed.

3. The portable ovulation testing apparatus as claimed in claim 1, wherein the diameter of the diaphragm is selected to provide the necessary depth of focus to the eyepiece so as to accommodate users with normal vision, as well as those with long/short sighted vision of up to plus/minus 4 diopters.

4. The portable ovulation testing apparatus as claimed in claim 2, wherein the plano-convex field lens is made of glass.

5. The portable ovulation testing apparatus as claimed in claim 2, wherein the plano-convex field lens is made of plastic and is attached to a polished plano-plano glass plate using transparent optical cement, to resist deviation/warping of the plastic lens, and offering a hard exterior glass surface upon which the biological specimen is disposed, and to enable repeated cleaning.

6. The portable ovulation testing apparatus as claimed in claim 1, wherein the fixed focus eyepiece includes a lens holder with means for maintaining the separation of the lenses sealed therein to form the fixed focus eyepiece assembly.

* * * * *